(12) United States Patent
Van Roy et al.

(10) Patent No.: US 8,999,183 B2
(45) Date of Patent: Apr. 7, 2015

(54) FABRICATION OF CONDUCTING OPEN NANOSHELLS

(75) Inventors: Willem Jozef Katharina Van Roy, Bierbeek (BE); Jian Ye, Leuven (BE); Pol Van Dorpe, Spalbeek (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 395 days.

(21) Appl. No.: 13/608,857

(22) Filed: Sep. 10, 2012

(65) Prior Publication Data

US 2013/0028840 A1    Jan. 31, 2013

Related U.S. Application Data

(62) Division of application No. 12/812,021, filed as application No. PCT/EP2009/052397 on Feb. 27, 2009, now abandoned.

(60) Provisional application No. 61/032,632, filed on Feb. 29, 2008.

(51) Int. Cl.
| | |
|---|---|
| *B44C 1/22* | (2006.01) |
| *G01N 21/65* | (2006.01) |
| *B22F 1/00* | (2006.01) |
| *B22F 1/02* | (2006.01) |
| *B82Y 30/00* | (2011.01) |

(52) U.S. Cl.
CPC ............ *G01N 21/658* (2013.01); *B22F 1/0018* (2013.01); *B22F 1/025* (2013.01); *B82Y 30/00* (2013.01); *B22F 2001/0029* (2013.01); *Y10S 977/958* (2013.01)

(58) Field of Classification Search
CPC  B44C 1/227; B82C 2201/0132; B82Y 30/00; B82Y 40/00; B82Y 20/00; B82Y 5/00; B82Y 15/00; B22F 1/0018; B22F 1/025; B22F 2001/0029; G01N 21/658
See application file for complete search history.

(56) References Cited

U.S. PATENT DOCUMENTS 6,660,381 B2    12/2003  Halas et al.
2002/0160195 A1 *  10/2002  Halas et al. ................... 428/403

FOREIGN PATENT DOCUMENTS

| EP | 2 249 985 B1 | 11/2012 |
| JP | 2006198641 | 8/2006 |

(Continued)

OTHER PUBLICATIONS

File History for EP Application No. 09714138.6 as of March 18, 2014, Now EP 2 249 985 B1.
Liu et al., Jap. Journ. of Appl. Phys. 45 (22), 2006, L582-L584.

(Continued)

*Primary Examiner* — Lan Vinh
*Assistant Examiner* — Jiong-Ping Lu
(74) *Attorney, Agent, or Firm* — Knobbe Marten Olson & Bear LLP

(57) ABSTRACT

A method involving ion milling is demonstrated to fabricate open-nanoshell suspensions and open-nanoshell monolayer structures. Ion milling technology allows the open-nanoshell geometry and upward orientation on substrates to be controlled. Substrates can be fabricated covered with stable and dense open-nanoshell monolayer structures, showing nanoaperture and nanotip geometry with upward orientation, that can be used as substrates for SERS-based biomolecule detection.

8 Claims, 11 Drawing Sheets

(56) References Cited

FOREIGN PATENT DOCUMENTS

| | | |
|---|---|---|
| WO | WO02059226 | 8/2002 |
| WO | WO2006135393 | 12/2006 |

OTHER PUBLICATIONS

Zheng et al., J. of Non-crystalline Solids 352, 2006, 2532-2535.
Correa-Duart et al., Advanced Materials 2005 (17), 2014-018.
Hirsch et al., Annals of Biomedical Engineering, vol. 34, No. 1, Jan. 1, 2006, 15-22.
Liu et al., Materials Science and Engineering B, vol. 140, No. 3, Jun. 15, 2007, 195-198.
Liu et al., Nanotechnology, vol. 16, No. 12, Dec. 1, 2005, 3023-3028.
Love et al., Nano Lett. 2 (8) 2002, 891-894.
Lu et al., Nano Lett. 5 (1), 2005, p. 119-124.
Oldenburg et al., J. Chem. Phys. Lett. 1998, 288, 243-247.

* cited by examiner

FABRICATION OF CONDUCTING OPEN NANOSHELLS

CROSS-REFERENCE TO RELATED APPLICATIONS

This application is a divisional of U.S. application Ser. No. 12/812,021, filed Jul. 7, 2010, which is the national phase under 35 U.S.C. §371 of prior PCT International Application No. PCT/EP09/052397 which has an International Filing Date of Feb. 27, 2009, which designates the United States of America, and which claims the benefit of U.S. Provisional Application No. 61/032,632, filed Feb. 29, 2008, the disclosures of which are hereby expressly incorporated by reference in their entirety and are hereby expressly made a portion of this application.

TECHNICAL FIELD OF THE INVENTION

The invention relates to the field of nanoparticles, in particular nanoparticles for use in sensor, drug delivery or imaging applications.

BACKGROUND OF THE INVENTION

Gold (Au) nanoshells are nanoparticles usually composed of a dielectric core, typically silica, coated with an ultrathin Au layer. These nanoparticles show interesting optical and chemical properties for the applications of surface-enhanced Raman spectroscopy (SERS) sensor, surface plasmon resonance (SPR) sensor, drug delivery, biomedical imaging and cancer therapeutics among others.

Reducing symmetry of Au nanoshells geometry shows interesting properties. It is possible to excite different plasmon modes in these particles when compared to standard particles. These particles show angle dependent plasmon resonance. This unique property may lead to a new class of optically active nanoparticles that can be manipulated by applied static or frequency dependent electric, magnetic, or optical fields. The particles enhance the electric field intensity coming out of the particles when compared to fully covered particles, i.e. particles whose symmetry has not been reduced.

Several groups have developed and demonstrated reduced-symmetrical nanoshells such as nano half-shells, nanocups, nanomoons and nanoeggs for SERS applications. Reduced-symmetrical nanoshells have been prepared before in various ways including electron-beam evaporation (EBE) and electroless plating. By these methods, the reduced-symmetrical structures of nanoshells, such as nanoaperture or nanotip, are usually oriented randomly or with their aperture downward, which obviously limits the molecular binding to the electric field enhanced regions in SERS applications. The Raman enhancement factors differ from place to place on a substrate because of the random orientation of reduced-symmetrical structures.

U.S. Pat. No. 6,660,381 describes a method for the fabrication of composite particles containing metal shell layers, i.e. a partial metal coverage. This fabrication method does not allow good control of the orientation and the geometry of the open-nanoshells.

WO2006135393 shows a method and a system for optimized surface enhanced Raman scattering comprising a support with on top nanoparticles having a shell surrounding a core. The local electromagnetic field around complete shells is lower when compared to the local electromagnetic field around the open-nanoshells.

WO2002059226 describes the fabrication of metal nanoshells having partial coverage of a substrate.

JP2006198641 describes an ion-beam processing method for forming nano-order convex portions.

Y. B. Zheng et al (J. of Non-crystalline Solids 352, 2006, p 2532-2535 describe the fabrication of ordered nanoring arrays for nanoscale optical sensors. This fabrication method does not allow good control of the geometry of the open-nanoshells.

J. Liu et al (Jap. Journ. Of Appl. Phys. 45 (22), 2006 p L582-L584 describe the fabrication of 2-dimensional arrays of hollow metal nanoshells on a substrate. This fabrication method does not allow good control of the geometry of the open-nanoshells.

M. A. Correa-Duarte et al (Advanced Materials 2005 (17), p 2014-2018) describe a method to fabricate asymmetric nanoshells with/without a core. This fabrication method does not allow good control of the orientation of the open-nanoshells.

Lu et al. (Nano Lett. 5 (1), 2005, p 119-124) present the fabrication of Au moon structures for the enhancement of a local electrical field at the edge area. This fabrication method does not allow good control of the orientation of the open-nanoshells.

J. C. Love et al (Nano Lett. 2 (8) 2002, p 891-894) describe the fabrication of silica core particles covered with Au on a substrate. This fabrication method does not allow good control of the orientation and the geometry of the open-nanoshells.

SUMMARY

It is an object of the present invention to present a method to fabricate open nanoshells with a well-controlled geometry either on a substrate or dispersed in a solvent. This method permits fabricating substrates covered with open nanoshells with well-controlled geometry and orientation. The above objective is accomplished by a method and device according to the present invention.

Over prior art materials using cores of polystyrene beads with diameters of 100 nm or more, the present invention is more versatile providing much smaller cores and a better control of the apertures.

In a first aspect, the present invention relates to a substrate covered with open nanoshells also called open shell nanoparticles or nanoshell particles with reduced symmetry (i.e. less symmetrical than spherical nanoparticles), said open shell nanoparticles comprising a dielectric core and a conducting layer partially surrounding said dielectric core, the uncovered part of the dielectric core being located at a side essentially opposite to the side of the substrate (i.e. at a side essentially opposite to the side of the substrate adjacent to said open shell nanoparticles).

In an embodiment of the first aspect, the uncovered part of the dielectric core may be at a side essentially opposite to the substrate, the edge of the conducting material being in a "cutting plane" making an angle between 0° and 45° with the plane of the substrate.

In an embodiment of the first aspect, the uncovered part of the dielectric core may be between 45% and 5% of the total surface area of the dielectric core.

In an embodiment of the first aspect, said dielectric core may be a material comprising air or $SiO_2$ and wherein said conducting layer comprises at least one material selected from the group consisting of Au, Ag, and Al. In SERS applications a higher field enhancement is obtained with silver when used with a plasma, but silver oxidises, whereas gold doe not. With air as the dielectric core, the capacity of the open shell nanoparticles to receive molecules increases, the contact area with the molecules increases and higher fields become accessible.

In an embodiment of the first aspect, a functionalisation layer for immobilising said open shell nanoparticles may be further present on said substrate.

In an embodiment of the first aspect, the substrate may be covered with at least one layer of open shell nanoparticles in an optimal packing resulting in up to 90% of the surface area being covered in the case of nanoparticles of identical size if viewed perpendicularly to a planar substrate.

In a second aspect, the present invention relates to a method for fabricating open nanoshells or open shell nanoparticles or nanoparticles with reduced symmetry said method comprising the steps of fabricating a plurality of dielectric cores;
depositing a conducting layer on said dielectric cores, thereby creating nanoshells or nanoshell particles;
selecting a substrate;
depositing said nanoshells on said substrate thereby forming a layer of nanoshells on said substrate;
removing part of said conducting layer from said nanoshells at a side essentially opposite of said side of the substrate adjacent to said nanoshells thereby creating a layer of open nanoshells.

In an embodiment of the second aspect, removing part of said conducting layer may be obtained by a directional etching technique.

In an embodiment of the second aspect, said directional etching technique may be ion milling.

In an embodiment of the second aspect, the method may further comprise functionalisation of said substrate prior to depositing said nanoshells on said substrate.

In an embodiment of the second aspect, the method may further comprise removing said dielectric core from said open nanoshells.

In an embodiment of the second aspect, the method may further comprise removing said open nanoshells from said substrate, for example by redispersing in solution.

In a third aspect, the present invention relates to a substrate obtainable by a method according to the second aspect.

In a fourth aspect, the present invention relates to the use of a substrate according to the first or fourth aspect in an imaging application, with an optical spectroscopy technique such as SERS-based biomolecule detection being preferred.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DESCRIPTION OF ILLUSTRATIVE EMBODIMENTS

Figure 1:
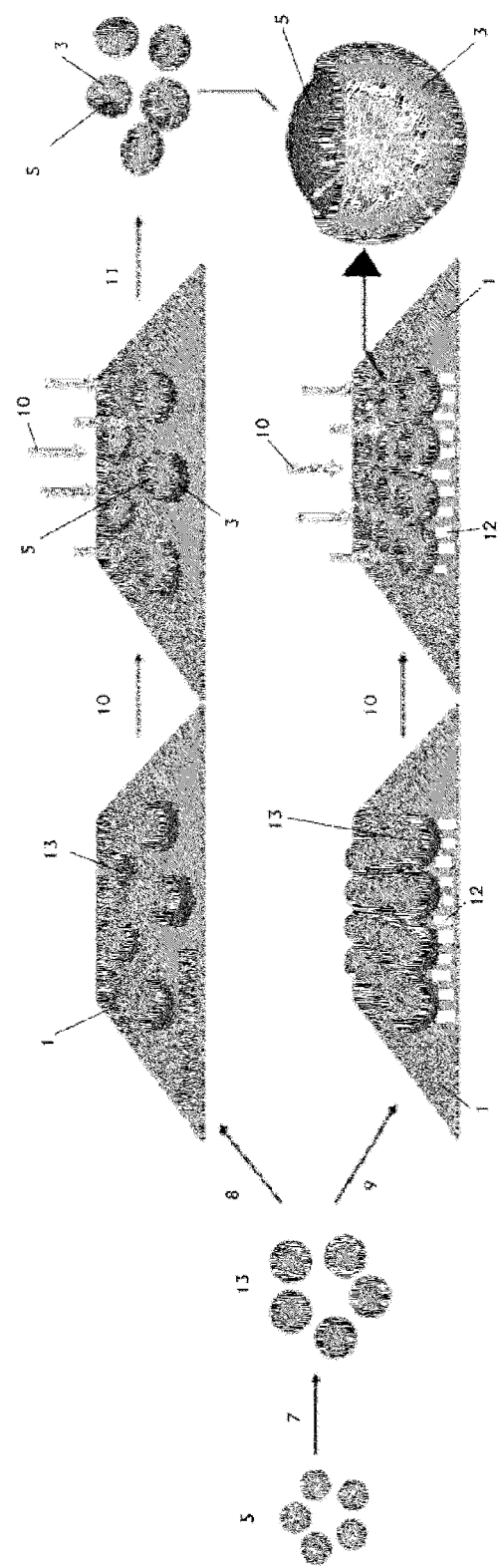
FIG. 1 shows a fabrication method for making open-nanoshells (e.g. Au open nanoshells) suspensions and monolayer structures according to embodiments of the present invention. The dimension of open-nanoshell particle is shown in the figure. r is the diameter of the core, R is the diameter of total particle, H is the height of non-removed shell of the open-nanoshell.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.

As used herein and unless stated otherwise, the term "nanoshell" or "nanoshell particle" relates to a nanoparticle with a dielectric core (e.g. $SiO_2$, polystyrene, . . . ) and complete conducting layer (e.g. a metal such as, Au, Ag, Al, . . . , or a semiconductor such as Si, GaAs, . . . ) around the core.

As used herein and unless stated otherwise, the term "nanoshell particle with reduced symmetry", or "open nanoshell", or "open shell nanoparticle" relates to a nanoparticle with a dielectric core and non-complete or partial conducting layer around the core.

As used herein and unless stated otherwise, the term "nanoring" relates to a substrate supported ring or toroidal-shaped nanostructure.

As used herein and unless provided otherwise, the term "nanoaperture" relates to an aperture made in a open-nanoshell.

As used herein and unless provided otherwise, the term "nanotip" relates to any sharp asperity at the edge of a nanoaperture.

As used herein and unless provided otherwise, the term "functionalisation molecule" relates to molecules able to attach to both, the substrate surface and the nanoshell particles.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

DETAILED DESCRIPTION

In a first aspect, the present invention relates to a substrate having a layer thereon, said layer comprising or consisting of nanoparticles, said nanoparticles comprising an open conductive shell. The nanoparticles may be monodisperse providing greater reproducibility, or have a broad size distribution providing wider resonances. The material of the substrate is not a limiting feature of the present invention and can comprise dielectric, semi-conducting or conducting materials. Examples of dielectric materials suitable for the substrate comprise but are not limited to glass, quartz, mica, $Si_3N_4$, $Al_2O_3$ and polymers among others. Examples of semi-conducting materials suitable for the substrate comprise but are not limited to Si, Ge, GaAs, group IV semi-conducting materials, group III-V semi-conducting materials, group II-VI semi-conducting materials and chalcopyrite among others. Examples of conductive materials suitable for the substrate comprise but are not limited to metals (such as Au, Ag and Cu among others) or doped semi-conductors such as ITO (e.g. on glass). Functionalised materials (i.e. materials having a surface bearing a layer of functionalisation molecules able to attach to both, the substrate surface and the nanoparticles) such as functionalized Si, or other materials are also suitable. In embodiments, the substrate may be a planar substrate, a curved substrate or any other surface shape. Preferably, the substrate comprises a planar surface.

In an embodiment of the present invention, the layer consist of the open shell nanoparticles. In certain embodiments of the present invention, the open shell nanoparticles are not embedded. In other embodiments, a matrix linking the open shell nanoparticles together is present, the layer comprising nanoparticles and a matrix. The matrix can be any material able to act as a binder between the nanoparticles. Preferably, the matrix is a polymer matrix any polymer with binding properties to being suitable, although translucent or transparent polymers are preferred. In yet another embodiment, the layer comprises open shell nanoparticles and functionalisation molecules at the interface with the substrate surface. Examples of adhesion (i.e. functionalisation) molecules comprise but are not limited to organosilanes, preferably organosilanes comprising a thiol or dithio function such as 3-mercaptopropyl-trimethoxysilane (MPTMS) or 3-mercaptopropyl-triethoxysilane (MPTES), among others. The functionalisation molecule may form a functionalisation layer on the substrate and may immobilize the nanoparticles on said substrate. In other words, to improve the stability and degree of coverage of the substrate, nanoshells can be immobilized on the substrate by using chemical functionalization such as a mercaptosilane functionalization, for example on a mercaptosilane functionalised ITO-coated glass or Si slide. The layer of open nanoshells can consist in nanoshells or comprise nanoshells. If it consists in nanoshells, the thickness of the layer is preferably equivalent to the dimension of the nanoshells, i.e. the layer is preferably a monolayer. If the layer comprises both nanoshells and a matrix within which the nanoshells are embedded, the thickness of the layer is also preferably equivalent to the dimension of the nanoshells and preferably smaller than twice this dimension so that a monolayer is formed. Open-nanoshells, for example Au open nanoshells, can be loosely packed or densely packed to form a monolayer with coverage on the substrate between 10% and 30%, or between 30% and 60% or between 60% and 80%, in the best case more than 80% and at most 90%. The coverage can be tuned from 10% to 80% or more (and up to 90%) by the concentration of nanoshells suspension. Part of the free space present between open-nanoshells is due to spatial limit (i.e. due to the spherical geometry of the particles theoretically limiting the coverage to $\pi/\sqrt{12}$ in the case of perfect spheres of identical size packed hexagonally) and the additional part of the free spaces present between open-nanoshells is possibly due to the incomplete functionalization of the substrate (when the substrate is functionalised). A higher degree of coverage can be obtained by using bimodal or very broad size distributions of the nanoparticles.

In a further embodiment of the present invention multilayers of open shell nanoparticles on a substrate are provided. Such multilayers can, for example, be built up layer by layer and may provide field confinement effects and optical field enhancement.

The open shell nanoparticles comprise a conductive open shell, i.e. a conductive shell comprising an opening. They can have any shapes such as spheroidal or cuboidal. Preferably, they are substantially spherical. The conducting layer (i.e. the shell) can be made of a metallic material (such as gold (Au), silver (Ag), nickel (Ni), titanium (Ti), aluminum (Al), copper (Cu) or platinum (Pt) amongst others), a semi-metallic material, or a (preferably doped) semiconducting material (such as Si or GaAs amongst others) or any other conducting material used in the field. Preferably, the core and the shell are made of different materials and the core is a dielectric and the shell a conductive material. Preferred conductive materials are metals and doped semi-conductors. More preferably, the conductive material is a metal wherein gold, silver and aluminium are most preferred. The conducting layer can be made of a single conducting material or can comprise different conducting materials, for example selected from the list above. In embodiments, the conductive open shell comprises at least on material selected from the group consisting of Au, Ag and Al. Most preferably, the shell is made of gold. Shells of various thickness are suitable. The thickness of the conducting layer or nanoshell layer can be from 5 nm to 100 nm, from 7 nm to 50 nm or from 10 nm to 30 nm, or from 10 nm to 100 nm. The part of the core that is not covered with conducting material (i.e. the uncovered part) can be varied between 70% and 1% if a movable ion source is used in the etching process, with between 60% and 5% being preferred, between 50% and 5% being particularly preferred, between 45% and 5% being especially preferred, between 40% and 5% being particularly especially preferred, between 30% and 5% being even more preferred, between 20% and 5% being still more preferred, between 20% and 10% of the total surface area of the core being yet still more preferred. In the case of a hollow nanoshell (i.e. nanoshells whose core has been removed), the part of the shell removed during directional removal or etching can be varied between 70% and 1% if a movable ion source is used in the etching process, with between 60% and 5%, being preferred, between 50% and 5% being particularly preferred, between 45% and 5% being especially preferred, between 40% and 5% being particularly especially preferred, between 30% and 5% being even more preferred, between 20% and 5% being still more preferred, and between 20% and 10% of the total original surface area of the shell being yet still more preferred. In embodiments, the surface area of the shell removed during the directional etching step is from 5 to 45% of the surface area of the shell. The open nanoshells may or may not have a dielectric core. The core is preferably made of a dielectric material and can comprise e.g. silicon dioxide ($SiO_2$) (e.g. the core particles used to make the nanoparticles can be silicon dioxide colloids), polymers such as polystyrene, magnetic materials such as $Fe_2O_3$, or other magnetic oxides. The core particles can be made of one material or can comprise several materials that can for instance be selected from the list above. When the core comprises more than one material, it is possible that it comprises both, conductive and dielectric materials if the outer surface of the core is dielectric. For instance, the core could be made of a conductive kernel coated with a dielectric coating. The important factor being that at least the outer surface of the core is a dielectric. Preferably, the core comprises (or consists of) $SiO_2$, silica having the additional advantage of being etchable. The shape of the core is preferably the same as the shape of the shell. Nanoshells of various core sizes are suitable. In an embodiment, the open nanoshells comprise a dielectric core partially surrounded by a conductive open shell.

The open nanoshells are oriented on the substrate in such a way that a majority, preferably 90% or more, most preferably substantially all of the open nanoshells have their opening directed away from the substrate (i.e. their opening do not touch the substrate, i.e. their opening is away from the substrate). In embodiments, if an arrow would be traced from the center of the particle to the center of the opening, this arrow would not point to the substrate and would preferably point away from the substrate. For instance, this arrow would make an angle of from 0 and 90° with the substrate, preferably 45 to 90°. In other words, said nanoparticles have the center of their shell open part at the half (or side) of the nanoparticles opposite to the half (or side) of said nanoparticle adjacent to said substrate.

In embodiments, the substrate comprises a planar surface on which the layer comprising nanoparticles is layed. The use of directional etching techniques permits to obtain open nanoparticles wherein the edges of the conductive open shell are approximately in a plane. Preferably this plane is making an angle between 45° and 90° with the plane of the substrate planar surface. Angles less than 90° provide a tilting effect with resulting improvement in turbulence during the wetting process with improved wetting as a result. In other words the opening of the open nanoshell is obtainable by etching said shell with a directional etching source (i.e. a non-isotropic flux of etching agent) making an angle of from 45 to 90° with the substrate planar surface. Expressed differently, when a core is present, the part of the core that is not covered with conducting material (the uncovered part) is at a side essentially opposite to the substrate. Depending on the angle of the substrate with respect to the directional etching (in case of ion milling the angle of the substrate with respect to the ion beam), the orientation of the open part of the nanoshells with respect to the substrate may change. The angle between a plane ("cutting plane") comprising the edge of the conducting material and the plane of the substrate can be between 0° and 90°, between 0° and 60°, between 1° and 60°, between 0° and 50°, between 2° and 50°, between 0° and 45°, between 3° and 45°, between 0° and 40°, between 4° and 40°, between 0° and 30°, between 5° and 30°, between 0° and 20°, between 5° and 10°.

Figure 11:
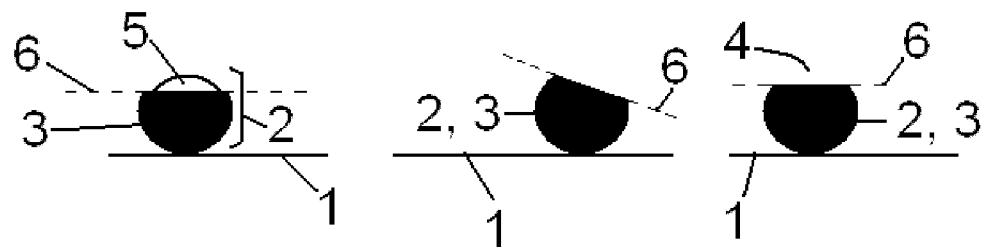
FIG. 11 is a diagrammatic illustration of various embodiments of the present invention.

FIG. 11 shows three substrates according to embodiments of the present invention. On the left side of FIG. 11, an open nanoshell (2) is represented laying on a substrate (1). The open nanoshell comprises a conductive open shell (3) and a dielectric core (5). The angle between a plane ("cutting plane") (6) comprising the edge of the conducting material (3) and the plane of the substrate (1) is 0°. The substrate represented in the centre of FIG. 11 has a conductive open nanoshell (2, 3) laying thereon. This open nanoshell does not comprise a core (i.e. it is hollow). The plane (6) comprising the edge of the conducting material (3) makes an angle comprised between 0 and 45° with the substrate. The substrate represented on the right side of FIG. 11 has an open nanoshell (2, 3) thereon represented laying on a substrate (1). The open nanoshell comprises a conductive open shell (3) and no dielectric core (5). The opening (4) of the open nanoshell is facing away from the substrate and the angle between the plane ("cutting plane") (6) comprising the edge of the conducting material (3) and the plane of the substrate (1) is 0°.

Substrates according to embodiments of the present invention with their open nanoshells layer (preferably monolayer) structures offer a stable and high density arrangement of open nanoshells on a substrate for various sensing application such as for instance surface-enhanced Raman scattering (SERS)-based biomolecules detection. In other words, embodiments of the present invention provide substrates topped with a layer of densely packed conductive open nanoshells which is stable, i.e. well attached to the substrate (when a chemical functionalisation is present between the conductive open nanoshells and the substrate). In particular, nanoshells with a small core size (<100 nm) and a thin shell thickness (<10 nm) having a relatively small particle size and having an optical response in near-infrared (NIR) region, are advantageously used in several applications, such as the biomedical imaging and thermotherapy for certain tumours.

In a second aspect, the present invention relates to a method for fabricating a substrate according to the first aspect of the present invention. In embodiments, the present invention relates to a method for fabricating a monolayer structure comprising conductive open nanoshells (such as e.g. gold nanoshells) on a substrate.

In embodiments, nanoparticles comprising a dielectric core and a conductive shell can first be prepared. Starting with dielectric core particles, a conductive layer can be deposited thereon. Deposition of the conducting layer can for example be done by seeding followed by electroless plating, or polymerization, or other chemical techniques. The surface roughness of the shells is mainly determined by the deposition technique used (e.g. the seeding and electroless plating process) to put the conducting layer on the core. That way, dielectric nanoparticles covered with a conducting layer can be prepared. Dimensions of open-nanoshells can be controlled by tuning core sizes and shell thicknesses in a broad range. The size of the core particles (i.e. the core size) can be from 50 nm to 2000 nm, from 60 nm to 1500 nm, or from 80 nm to 1000 nm and preferably from 80 nm to 400 nm. The thickness of the conducting layer (i.e. the nanoshell layer) can be from 5 nm to 100 nm, from 7 nm to 50 nm or from 10 nm to 30 nm, or from 10 nm to 100 nm. In embodiments, this method may comprise the steps of providing a layer as described in the first aspect on a substrate. Before deposition, the substrate can be treated, for example by cleaning with deionised water, piranha solution, UV ozone treatment, ultrasonication or any other method known in the art. In embodiments, prior to provide said layer on said substrate, the substrate may be chemically functionalised. Functionalisation can for instance be performed by applying an organosilane layer on the substrate surface. Deposition of the nanoshell layer can be done by drop-casting of nanoshells suspension, spin coating of nanoshells suspension, immersing functionalized substrate into nanoshells suspension, creating ordered monolayers, self-assembly, or other techniques well known to the person skilled in the art. The layer comprises or consists of nanoshell particles. Providing the layer on the substrate result in the forming of a layer of nanoshell particles on the substrate. In this aspect of the present invention, the nanoshell particles of the provided layer comprise a dielectric core and a conductive shell. In embodiments, the method according to the second aspect of the present invention comprises the step of depositing a layer on a substrate, said layer comprising nanoparticles, thereby forming a layer of nanoparticles on said substrate wherein said nanoparticles comprise a dielectric core and a conductive shell. Once the layer is provided on the substrate, part of the conductive shell, not in contact with the substrate surface, is removed. Preferably, part of the conductive shell is removed at the side of said nanoparticles opposite to the side of the nanoparticles adjacent to the substrate, thereby forming nanoparticles comprising a conductive open shell. In embodiments, the step of removing part of the conductive shell may be performed via a directional removing (e.g. directional etching technique) such as e.g. ion milling. Directional removing (e.g. etching) is advantageous as this allows removing (e.g. etching) the material at a place away from the substrate (e.g. only at the top side of the particles) thereby creating a layer of open nanoshells on the substrate, whereby at least 50% of the open nanoshells, preferably at least 90% of the open nanoshells, most preferably substantially all open nanoshells have substantially the same orientation. So, in embodiments, most or all open-nanoshells are "facing up" with the open part at the side opposite to the substrate. That way, open nanoshells layer (e.g. a monolayer thereof) structures can be obtained on the substrate.

The etching rate is material dependent, and depends on the etching technique, the system that is used and the operating conditions of the system. In embodiments, the method may be based on an ion-milling process for fabricating the open nanoshells and the monolayer structures comprising them. Although other methods such as resists techniques, or directional techniques such as mechanical abrasion e.g. scrubbing can also be used partly to remove the shell. An ion milling process will result afterwards in open-nanoshells layer (e.g. monolayer) structures on the substrate. Its intrinsic working principle makes ion milling a very directional etching method. By tuning the ion milling time, the amount of material removed from the nanoshells can be varied, thereby tuning the geometry of the open-nanoshell. Another advantage of ion milling is its excellent repeatability (i.e. reproducibility). In addition, ion milling is a facile, fast and clean technology to fabricate open-nanoshells.

The following parameters hold for the ion milling process. The ion milling time depends on the parameters used in the ion milling process (such as but not limited to gasses, ionisation efficiency and accelerating voltage). During ion milling the base pressure in the processing chamber can vary between $1.0\times10^{-7}$ mTorr and $1.0\times10^{-10}$ mTorr, or between $1.0\times10^{-8}$ mTorr and $1.0\times10^{-9}$ mTor, or even better below $8.0\times10^{-8}$ mTorr. In the ion milling process, typically a small amount of etching gas, for example Xe, Ar, or others, is introduced in the deposition chamber. The flow rate can vary between 0.5 sccm (Standard Cubic Centimeters per Minute) and 10 sccm, or between 1 and 5 sccm, for example 2.4 sccm for Xe. The gas is ionized by a filament under a large voltage, thereby creating ions. The voltage can be from 50V to 3000V, or from 100V to 1000V, or from 200V to 500V, typically 375 V. A large electric field then accelerates the ions towards a grid under a large negative bias. The bias voltage or accelerating voltage can vary between 50V and 3000V, or between 100V and 1000V, or between 200V and 500V, typically 400V. Before hitting the sample, the ion beam is neutralized by a cloud of electrons, generated by a plasma, for example Ar plasma, Xe plasma, or other. The flow rate of the gas used for creating the plasma can vary between 0.5 sccm and and 10 sccm, or between 1 and 5 sccm, for example 2 sccm in the case of Ar.

When the ions carry a large enough momentum they will knock out atoms from the sample. That way nanotip and nanoaperture structures can be fabricated on the open-nanoshells surface.

As mentioned before, the etch rate is material dependent, and depends on the etching technique, the system that is used and the operating conditions of the system. So the etching time, for example the ion milling time, can be different for different shell materials. The etch rate, for example in case of ion milling, can vary between 2 nm/min and 40 nm/min, typically between 10 nm/min and 35 nm/min. For a certain material the etch time, for example the ion milling time, can be tuned such as to remove a certain amount of material. The etch time, for example ion milling time, can be from 1 s to 200 s, or from 10 to 100 s or from 20 to 60 seconds. By tuning the etching time the part of the core that is not covered with conducting material (i.e. the uncovered part) can be varied between 70% and 1%, between 60% and 5%, between 50% and 5%, between 45% and 5%, between 40% and 5%, between 30% and 5%, between 20% and 5%, between 20% and 10% of the total surface of the core.

Figure 12:
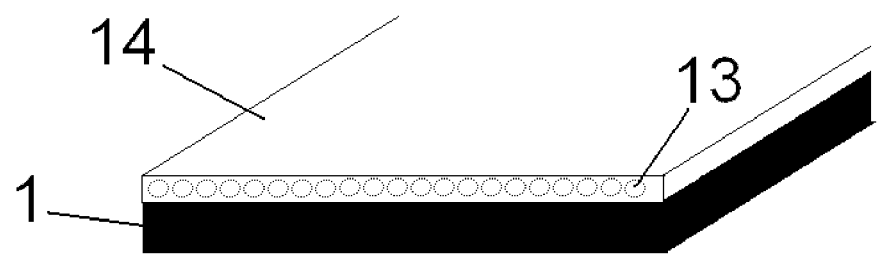
FIG. 12 illustrates a method for obtaining a substrate according to an embodiment of the present invention.
Figure 12:
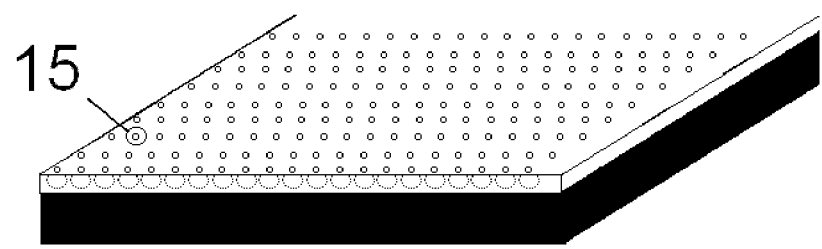

Instead of ion milling, other techniques such as chemically assisted ion beam etching (CAIBE), reactive ion etching (RIE), or others with similar directional etching behaviour, can be used. That way an etch chemistry can be chosen that etches the conducting material much faster than the conducting core, such that the conducting material can be etched highly selectively with respect to the dielectric core, thereby etching the conducting material while leaving the core unetched. An alternative directional removing technique suitable when the layer of nanoparticles is embedded in a matrix (e.g. a polymer matrix), is to mechanically remove (e.g. via scrubbing in a Chemical Mechanical Polishing) (CMP)-like process) an upper layer of the layer until the dielectric core of the particles is reached. This results in polymer layer comprising metallic spots or rings at its surface. This embodiment is illustrated in FIG. 12. At the top of FIG. 12, a substrate (1) having a layer (14), said layer comprising nanoshells (13) embedded in a matrix, is represented. The bottom of FIG. 12, shows the same substrate after that an upper layer of the layer (14) has been removed creating open nanoshells and making metallic spots or rings (15) apparent at the surface (14).

In embodiments, once part of the conductive open shell is removed, the method may further comprise a step of removing the dielectric core from the open shell nanoparticles. This results in a layer of hollow open nanoshells. The chemistry used for removing the core should preferably be chosen such that it can selectively remove the core without affecting much the conducting shell. Preferably, the chemistry used for removing the core should only remove the core and leave the open conducting shell intact. In the case of Au open-nanoshells with silica core for example, removing the silica core can be done by using aqueous HF for suspensions or vapor-phase HF for Au open-nanoshells monolayer structures. This keeps the Au open-nanoshells intact.

Methods according to embodiments of the present invention allow good control of the reduced-symmetrical geometry of the nanoparticles and allows monolayer structures to be realised with upward-oriented aperture on a substrate with good control and reproducibility. This makes the fabricated open nanoshells (e.g. Au open nanoshells) and substrate having a mono(layers) thereof suitable for a range of applications, for example, as active components in thermotherapy system and SPR biosensors. In particular, these particles with the features of nanoaperture optionally comprising nanotip structures can be good substrates for optical spectroscopy techniques such as surface-enhanced Raman scattering (SERS)-based molecule detection, or surface-enhanced resonance Raman scattering (SERRS), surface-enhanced coherent anti-Stokes Raman scattering (SECARS), surface-enhanced infrared absorption (SEIRA), surface-enhanced fluorescence, surface-enhanced hyper-Raman scattering (SE-HRS).

Contrarily to the prior art, methods according to embodiment of the present invention using controlled material removal such as ion milling allow the open-nanoshells to have a feature of the open-structure (i.e. the aperture) uniformly upward-oriented on the substrate, implying an improved control of reduced-symmetrical structure's orientation. An advantage of most of these directional etching techniques, for example ion milling, is the reproducibility of the ion milling process. Ion milling technology allows the open-nanoshell geometry and upward orientation to be controlled. The open-nanoshells monolayer structures, being stable and dense structures, with nanoaperture and nanotip geometry, and having an upward orientation are good substrates for SERS-based biomolecules detection.

Figure 2:
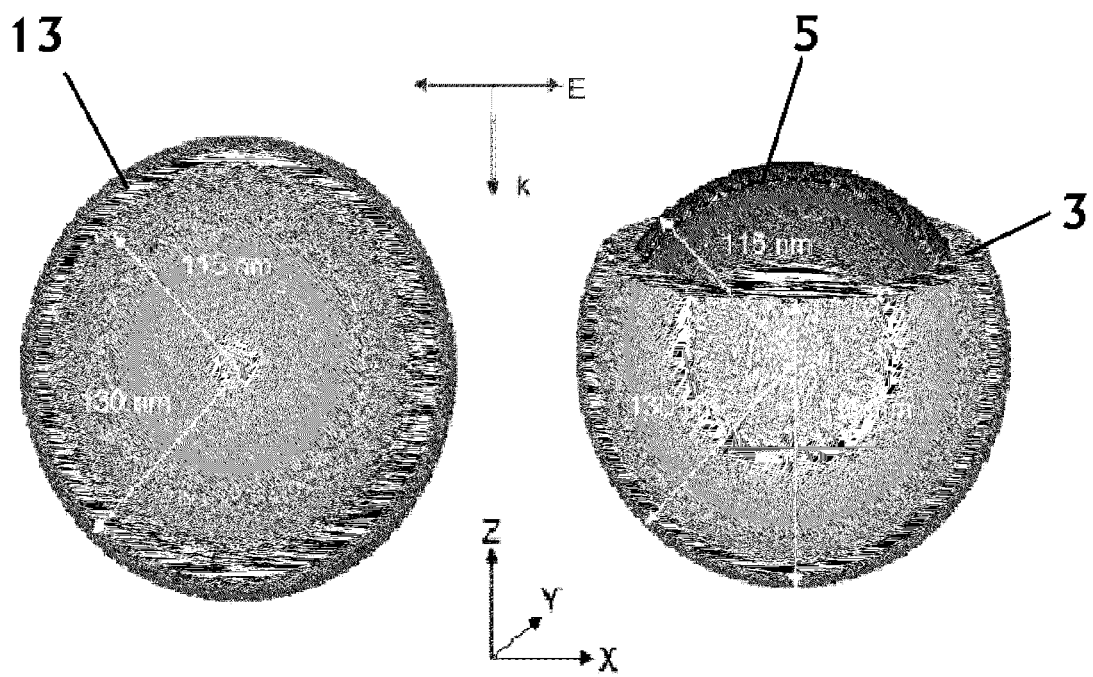
FIG. 2 is a scheme of the simulation system used in finite difference time domain (FDTD) calculations.

A benefit of the good control and reproducibility of these directional etching techniques, for example milling technology, is the fact that open-nanoshells with non-removed shell with different heights can be fabricated by tuning the amount of time under etching or ion milling. In other words, the height of the non-removed shell of the open-nanoshells, not taking the core into consideration, can be controlled by varying the directional removing time. This offers the capability to control the reduced-symmetrical geometry of open nanoshells (e.g. Au open-nanoshells). That way, different SPR wavelengths can be selected by making open-nanoshells with different heights of non-removed shell, H i.e. the perpendicular distance between the centre of the plane made by the edges of the remaining shell and the furthest extremity of the shell as shown in FIG. 2. The height, H, of the non-removed shell of the open-nanoshells is a parameter for controlling their optical properties.

In a further aspect of the present invention, a method is provided for producing open nanoshells involving the steps of the method of the second aspect of the present invention. Where a polymer matrix is not present, a last step of the method may consist in removing the open nanoshells from the substrate e.g. by dissolving away the optionally used functional layer or other means by which the open nanoshells adhere to the substrate, thereby obtaining unattached open nanoshells. If the removal step involved the use of a liquid such as water or solvent to remove any optional functional layer or other adhesive means, the free nanoshells so obtained may be dispersed or suspended in said liquid. In that case, the open-structure of the particles will be randomly orientated. The relatively small size and near-infrared (NIR) optical properties result in open-nanoshells suspensions suitable for the biomedical imaging and thermotherapy.

In embodiments, the present invention provides a method of fabricating Au (gold) open-nanoshells suspensions.

In embodiments, the present invention also provides for the use of open nanoshells removed from the substrate in the treatment of medical conditions by thermotherapy, in biomedical imaging and as SPR biosensors.

FIG. 1 shows a method of fabrication of open-nanoshells according to an embodiment of the present invention. First, nanoshells (13) comprising a core (5) and a shell (3) can be prepared. The dimensions of open-nanoshell particle are shown in FIG. 1: "r" is the diameter of the core (5), "R" is the diameter of total particle (and also the diameter of the shell (3)), "H" is the height of non-removed part of the open-nanoshell (3). For this purpose dielectric core particles (5) are selected.

On top of these core particles (5) (i.e. around said core particles) a conducting layer (3) can be deposited (7) leading to the formation of nanoshells (13).

In a next step, nanoshells (13) are deposited (e.g. directly without the pre-deposition of a chemical functionalisation layer (12) on the substrate (1) (path (8)) or after deposition of a chemical functionalisation layer (12) (path (9)) (e.g. from a suspension) onto a substrate (1). The substrate (1) can be functionalised with e.g. a monolayer of organic adhesion molecules (12) in order to immobilize the particles (13). To create open-nanoshells (3+5), directional etching (10) of the conducting layer (3) of the nanoshells (13), for example by ion milling, can be done on the nanoshells (13) deposited on the substrate (1). Since the electric field enhanced regions are mostly located on the surface or the sharp edge of nanoaperture or nanotip structures, the cores (5) of the open-nanoshells can be preserved.

However, it is also possible to remove the core (5). Afterwards, the particles can be redispersed (11) (e.g. ultrasonically) in a liquid medium, for example in water.

Example 1

First, Au nanoshells with various core sizes and shell thicknesses were prepared by seeding and electroless plating from silica colloids. Au nanoshells were synthesized according to a modified method of Oldenburg et al [J. Chem. Phys. Lett. 1998, 288, 243-247]. Monodisperse silica nanoparticles were synthesized by the hydrolysis of tetraethyl orthosilicate (TEOS) in basic solution via the Stöber process and functionalized with (3-aminopropyl)triethoxysilane (APTES) in ethanol during 12 hours. These functionalized silica particles were covered with dots of a thin Au colloid (1-2 nm) prepared by the method of Duff et al [Langmuir 1993, 9, 2301-2309]. A subsequent reduction of an aged mixture of 1% chloroauric acid ($HAuCl_4$) and potassium carbonate ($K_2CO_3$) by a solution of formaldehyde ($CH_2O$) or hydroxylaminemono hydrochloride ($H_2NOH.HCl$), resulted in a complete Au shell coverage on the nanoparticle surface. The resulting Au nanoshells were purified by repeated centrifugation and washing with deionized water and finally redispersed in deionized water.

Au open-nanoshells monolayer structures were fabricated by immobilizing Au nanoshells on a 3-mercaptopropyl-trimethoxysilane (MPTMS) functionalized ITO glass or Si substrate to improve the stability and coverage on the substrate. Scanning electron microscopy (SEM) showed that most of Au open-nanoshells were densely packed to form a monolayer with more than 80% coverage on the substrate.

The nanoparticles in the water solution were deposited on indium tin oxide (ITO)-coated glass or Si substrates. Prior to their use, ITO-coated glasses or Si substrates were cleaned by a piranha solution (1:3 (v/v) mixture of 30% by weight aqueous $H_2O_2$ and concentrated (98.6 wt %) $H_2SO_4$), rinsed well with deionized water and dried in a stream of $N_2$. Au open-nanoshells suspensions were typically prepared by drop-casting aqueous suspensions of Au nanoshells on an ITO-coated glass or Si substrate.

Au open-nanoshells suspensions and open-nanoshell monolayer structures were fabricated by using an in-house made ion miller system, using an energetic ion beam of Xe ions to bombard the sample surface thereby etching away sample material. Therefore, Au nanoshells on ITO glass or Si substrate were placed into the ion miller system.

Different ion milling times were used with the following parameters: 375 V beam voltage, 400 V accelerator voltage, 2.4 sccm Xe flow rate, 2 sccm Ar flow rate and below $8.0 \times 10^{-8}$ mTorr base pressure in the processing chamber. A small amount of Xe gas (2.4 sccm Xe flow rate) is introduces into the chamber which becomes ionized by a filament under a large voltage (375 V beam voltage). A large electric field (400 V) then accelerates the Xe ions towards a grid under a large negative bias (400 V accelerator voltage). Before hitting the sample, the ion beam is neutralized by a cloud of electrons generated by Ar plasma (2 sccm Ar flow rate and below $8.0 \times 10^{-8}$ mTorr base pressure). When the Xe atoms carry a large enough momentum they will knock out atoms from the sample. The etch rate is material dependent (e.g. 35 nm/min in case of Au). An advantage is the fact that it is a very directional etching method. When the beam of ions has a constant intensity, the milling depth is controlled by the amount of time the sample is being bombarded by the atoms.

To show the benefits of ion milling technology in the fabrication of Au open-nanoshells, open-nanoshells with different non-removed shell heights (FIG. 8) were fabricated by varying the amount of time under ion milling. The ion milling time was varied between 20 and 60 seconds with the parameters described above. This offers the capability to control the reduced-symmetrical geometry of Au open-nanoshells.

Afterwards, Au open-nanoshells were released from the slide into an aqueous suspension by ultrasonication.

Figure 5:
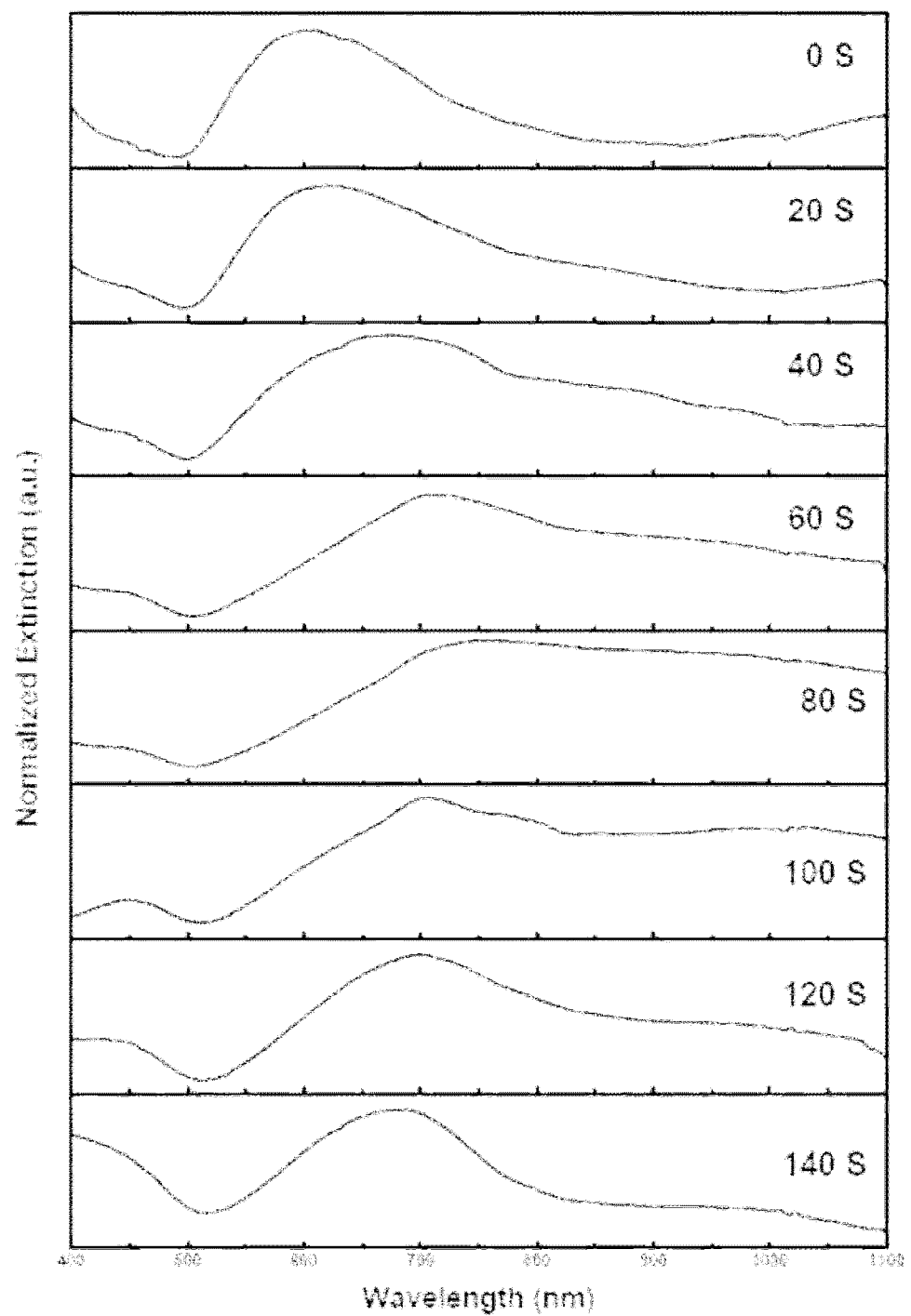
FIG. 5 shows optical extinction spectra of open-nanoshells, according to embodiments of the present invention, made by ion milling for different times nanoshells deposited on quartz in air by drop-casting.

Different SPR wavelengths have been detected in Au open-nanoshells with different non-removed shell heights as shown in FIG. 5. The height of the non-removed shell of Au open-nanoshells is a parameter to control their optical properties.

All ion milling experiments here have been performed repeatedly and the consistent results show excellent repeatability of ion milling technology.

TEM and AFM measurements confirm the nanoaperture and nanotip structures on the Au open-nanoshells obtained (FIGS. 6 and 7) allowing local electric field enhancement.

Figure 6:
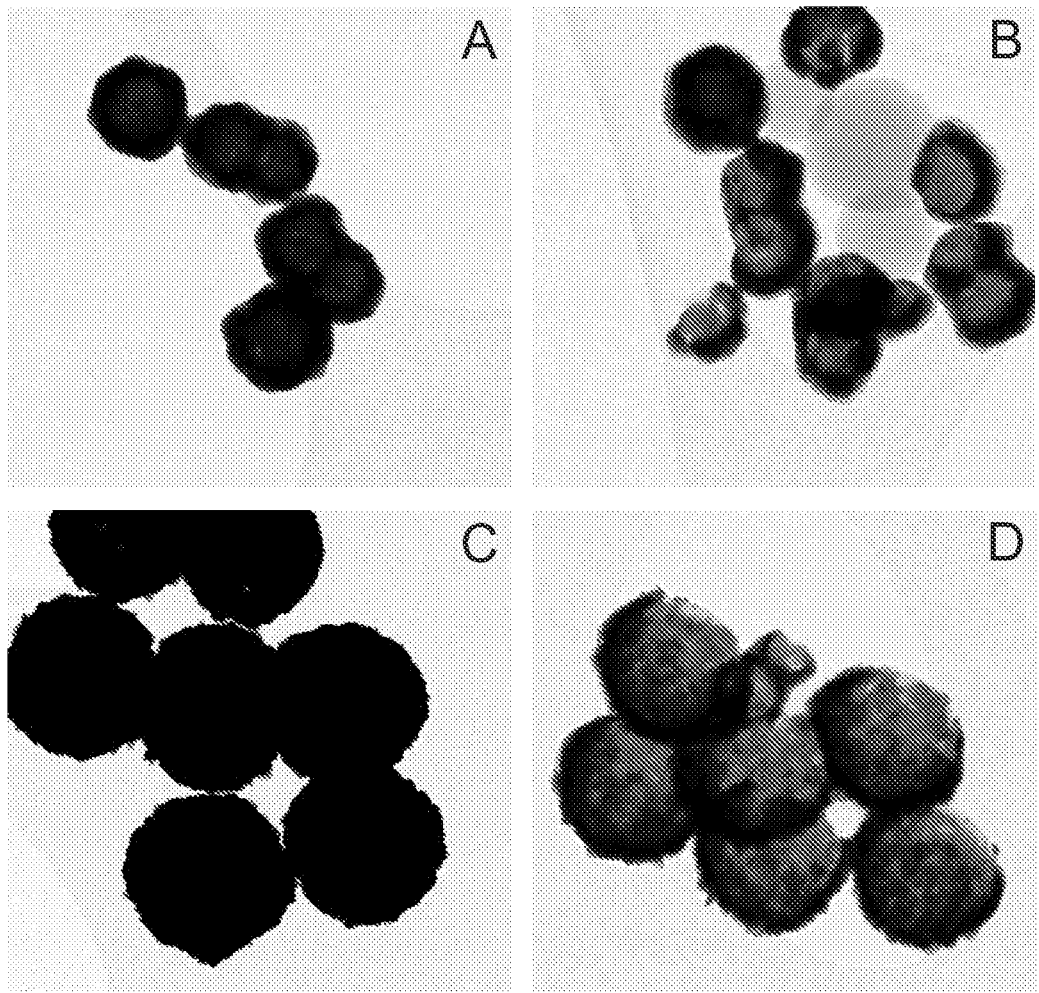
FIG. 6 shows TEM images of Au nanoshells (A: r/R/H=43/73/146 nm; C: r/R/H=115/130/260 nm) and Au open-nanoshells (B: r/R/H=43/73/109 nm; D: r/R/H=115/130/195 nm) according to embodiments of the present invention. Scale bars correspond to 100 nm.

Transmission electron microscopy TEM images were recorded on a 300 kV Philips CM30 instrument equipped with a field emission source. A drop of the aqueous Au nanoshells or open-nanoshells suspension was placed onto a carbon-coated copper grid (Holey Carbon, 300 mesh Cu) to dry at room temperature for TEM imaging. FIG. 6 shows TEM images of Au nanoshells (A: r/R/H=43/73/146 nm; C: r/R/H=115/130/260 nm and Au open-nanoshells (B: r/R/H=43/73/109 nm; D: r/R/H=115/130/195 nm). The dimensions of open-nanoshell particle are shown in FIG. 1: "r" is the diameter of the core, "R" is the diameter of total particle, and "H" is the height of the non-removed shell of open-nanoshells. Scale bars correspond to 100 nm. TEM images FIGS. 6 A and C have shown Au nanoshells with complete shells with different dimensions (core size and shell thickness). FIGS. 6 B and D have shown Au open-nanoshells with incomplete shells with different dimensions (core size and shell thickness) and different orientations.

Scanning electron microscopy (SEM) images of Au nanoshells deposited on an ITO-coated glass by drop-casting were taken using a Philips XL30 FEG instrument operated at an accelerating voltage of 5 kV. SEM images have shown that Au open-nanoshells with different dimensions and configurations can be prepared. Dimensions of open-nanoshells can be controlled by tuning core sizes and shell thicknesses in a broad range. The core size varied between 80 and 1000 nm and shell thickness can vary between 10 and 30 nm. In the top and side views, nanotip and nanoaperture structures were clearly observed on the open-nanoshells surface. The surface roughness of the shells was determined by the applied electroless plating procedure. All open-nanoshells were "facing up" with respect to the open-structures (i.e. the shell opening is facing away from the substrate).

Figure 8:
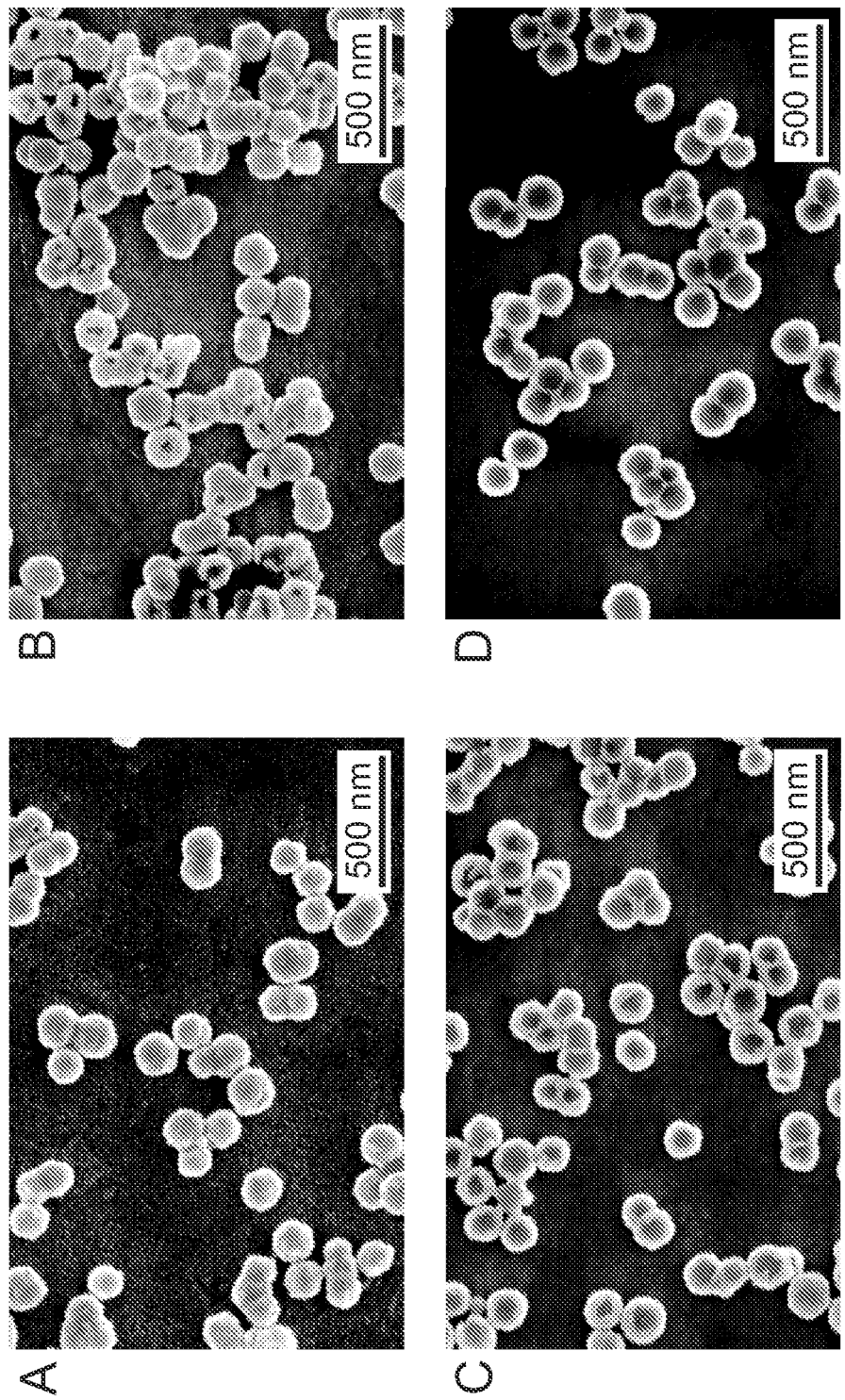
FIG. 8 shows SEM images of Au nanoshells (r/R/H=43/73/146 nm) on an ITO glass (A) before and after ion milling for (B) 20, (C) 40 and (D) 60 seconds according to embodiments of the present invention.

FIG. 8 shows SEM of Au nanoshells (r/R/H=43/73/146 nm) before ion milling (FIG. 8A) and after ion milling for 20 seconds (FIG. 8B), 40 seconds (FIG. 8C) and 60 seconds (FIG. 8D). From FIG. 8, it has been shown that open-nanoshells with different non-removed shell heights can be obtained by tuning the amount of time under ion milling. This is a way to precisely control the reduced-symmetrical geometry of Au open-nanoshells. Combining with FIG. 5, it is demonstrated that the height of the non-removed shell of Au open-nanoshells is a parameter to control their optical properties.

Figure 9:
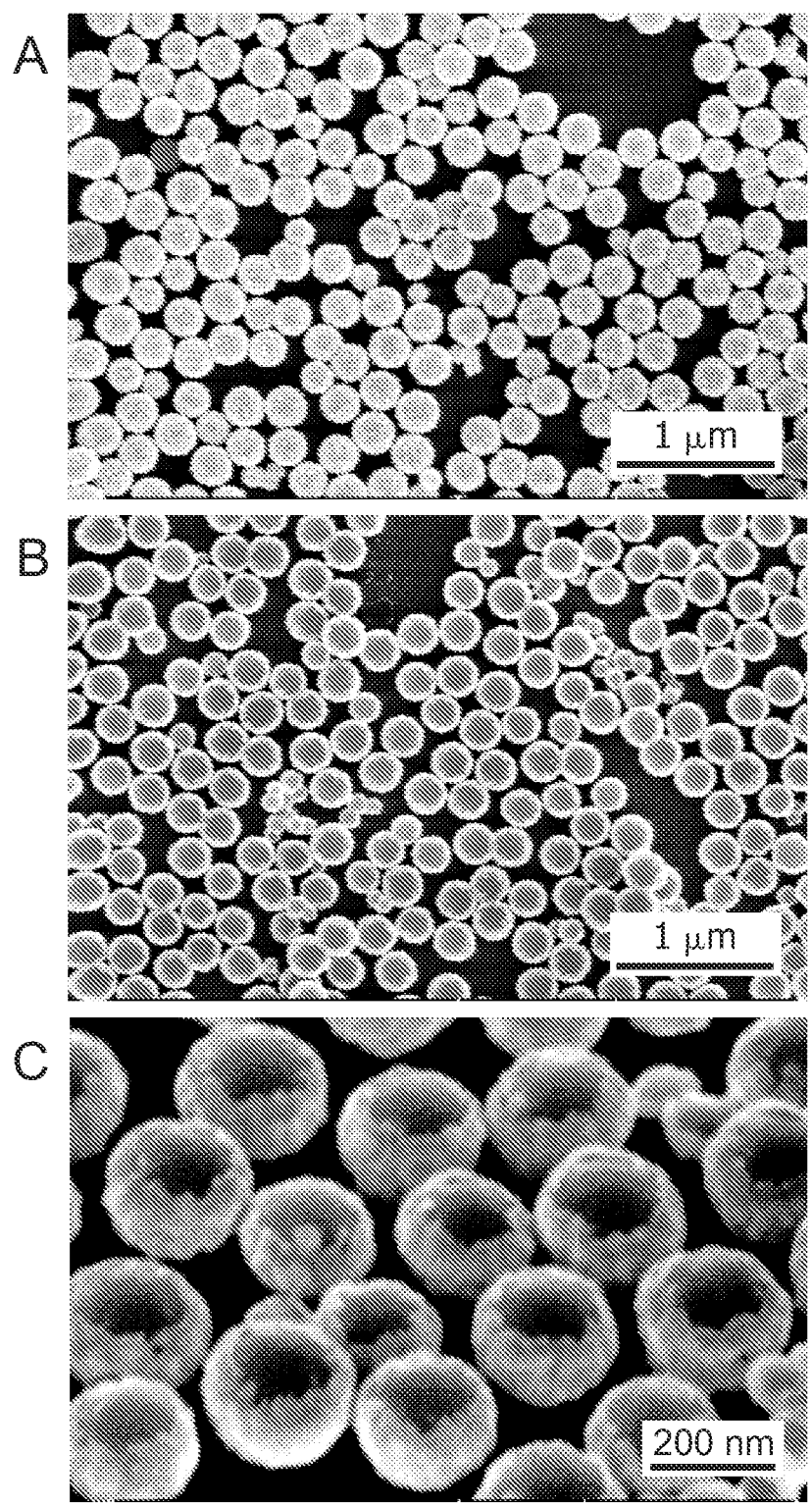
FIG. 9 shows SEM images of monolayer structures of Au nanoshells (r/R/H=115/130/195 nm) on a Si substrate (A) before and (B, C) after ion milling for 40 seconds (B: top view image; C: side view image) according to embodiments of the present invention.

FIG. 9 shows SEM images of monolayer structures of Au nanoshells (r/R/H=115/130/195 nm) (A) before and (B, C) after ion milling 40 seconds on a Si substrate (B: top view image; C: side view image). The dimensions of open-nanoshell particle are shown in FIG. 1: "r" is the diameter of the core, "R" is the diameter of total particle, and "H" is the height of the non-removed shell of the open-nanoshell. FIG. 9 (B, C) shows the open-nanoshells monolayer structures when a mercaptosilane functionalization is used. We observe the improvement of the stability and coverage of the monolayer structure on the substrate. Most of Au open-nanoshells were densely packed to form a monolayer with more than 70% coverage on the substrate. Part of the free space present between open-nanoshells is due to spatial limit (i.e. due to the spherical geometry of the particles theoretically limiting the coverage to $\pi/\sqrt{12}$ in the case of perfect spheres of identical size packed hexagonally) and the additional part of the free spaces present between open-nanoshells is possibly due to the incomplete functionalization of the substrate.

Figure 7:
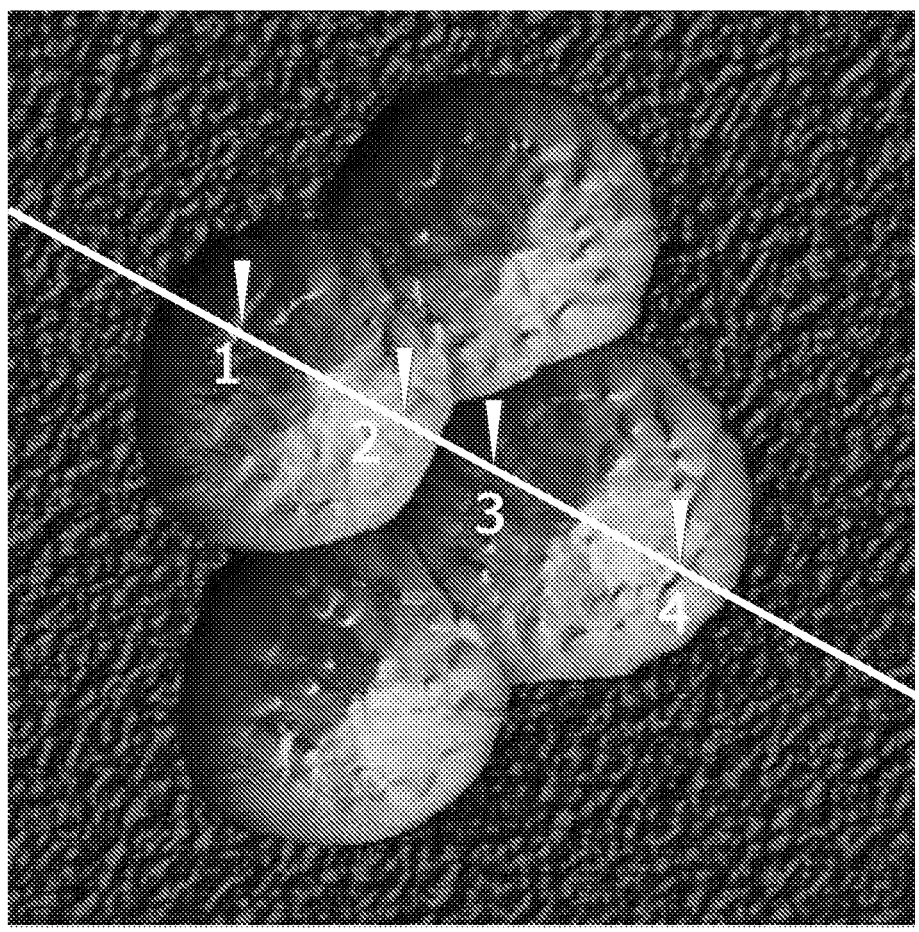
FIG. 7 shows the line-profile of an AFM image (1 μm×1 μm) of Au open-nanoshells on a Si substrate according to embodiments of the present invention.
Figure 7:
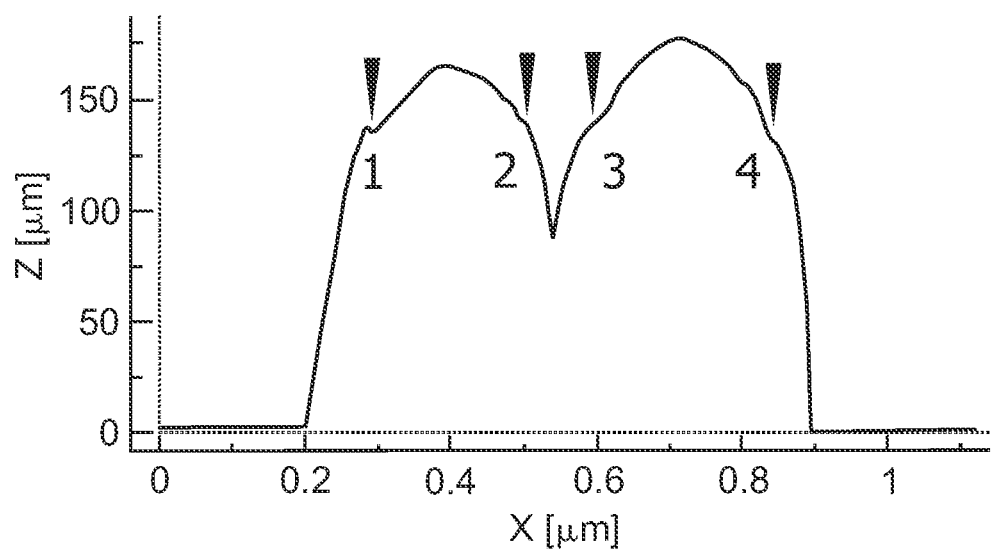

A drop of the aqueous Au open-nanoshells suspension was cast onto a Si substrate and then dried at room temperature for atomic force microscopy (AFM) scanning. AFM images were acquired in the tapping mode on a Dimension 3000/Nanoscope IV, VEECO, under ambient conditions with the scan rate between 0.4 and 0.5 Hz. Si cantilevers with a spring constant between 40 and 45 N/m were used at resonance frequencies between 250 and 350 kHz. The free amplitude peak is adjusted ~1 V. All images post-processing are performed using flatten order 1. FIG. 7 shows the rough surface of Au layer in open-nanoshell structure and furthermore confirms the nanoaperture and the nanotip structures on the Au open-nanoshells, which allows local electro-magnetic field enhancement. The line-profile In FIG. 7 of an AFM image (1 µm×1 µm) of Au open-nanoshells on a Si substrate shows the surface morphology of the open Au nanoshells more clearly.

Example 2

Finite Difference Time Domain Simulations

Simulations of optical extinction spectra and near-field distribution pictures were obtained based on the finite difference time domain (FDTD) simulations or FDTD method using the program FDTD Solutions (version 5.1) purchased from Lumerical Solutions, Inc., (Vancouver, Canada). The simulations were performed with the parallel FDTD option on a HP ProLiant DL145 G3 Server with 2 Dual-Core AMD Opteron 2000 processors at 2.8 GHz and 8 GB of RAM. The FDTD method is based on the numerical solution of the Maxwell's equations and can be used to obtain an adequate picture of the electromagnetic near-field distribution around the structures with arbitrary shapes.

The simulating system consists of a Au nanoshell or open-nanoshell. FIG. 2 shows a schematic representation of the simulating system used in FDTD calculations. In those simulations, the Au nanoshell or open-nanoshell was placed in air. The particle was illuminated with a total-field scattered-field (TFSF) source [S. Taney et al, Laser Phys. Lett. 2006, 3, 594-598], which propagates in the k=−Z direction. The direction of the electric field E was perpendicular to k and parallel to the X direction. The wavelength of incident light was varied from 400 nm to 1700 nm and the amplitude was set as 1. A perfect matched layer (PML) was used as radiation boundary condition. The simulation region is 800×800×800 nm$^3$ with a grid size of 3 nm. The whole simulation region was assumed in air. In these calculations, the dimensions (r/R/H) of the Au nanoshell and open-nanoshell were set as 115/130/260 nm and 115/130/195 nm, respectively. The dispersion model for Au derived from the experimental data provided by P. B. Johnson and R. W. Christy [Phys. Rev. B 1972, 6, 4370-4379] were used. The total complex-valued permittivity of the Au $\in(\omega)$ is modelled by the combination of a Drude and a Lorentz model, and hence results from the sum of three different material modes $\in_{REAL}(\omega)$, $\in_L(\omega)$ and $\in_P(\omega)$. $\in_{REAL}(\omega)$ is the basic background permittivity $\in_{REAL}$=6.8065. $\in_L(\omega)$ is the equation based on a Lorentz model $$\varepsilon_L(\omega) = \varepsilon_{LORENTZ} \frac{\omega_0^2}{\omega_0^2 - 2i\delta_0\omega - \omega^2}$$

with parameters $\in_{LORENTZ}$=1.6748, $\omega_0$=4.506608080759082×10$^{15}$ Hz, $\delta_C$=6.820216162455338×10$^{14}$ Hz, and $\in_P(\omega)$ is the equation based on the Drude model $$\varepsilon_P(\omega) = \frac{\omega_P^2}{i\omega\nu_C + \omega^2}$$

with parameters $\omega_P$=1.3538345417988594×10$^{16}$ Hz, $\nu_C$=1.068689183387936×10$^{14}$ Hz. This fit provides an accurate description of the dielectric data of Au in the wavelength range from 400 nm to 1700 nm.

Figure 3:
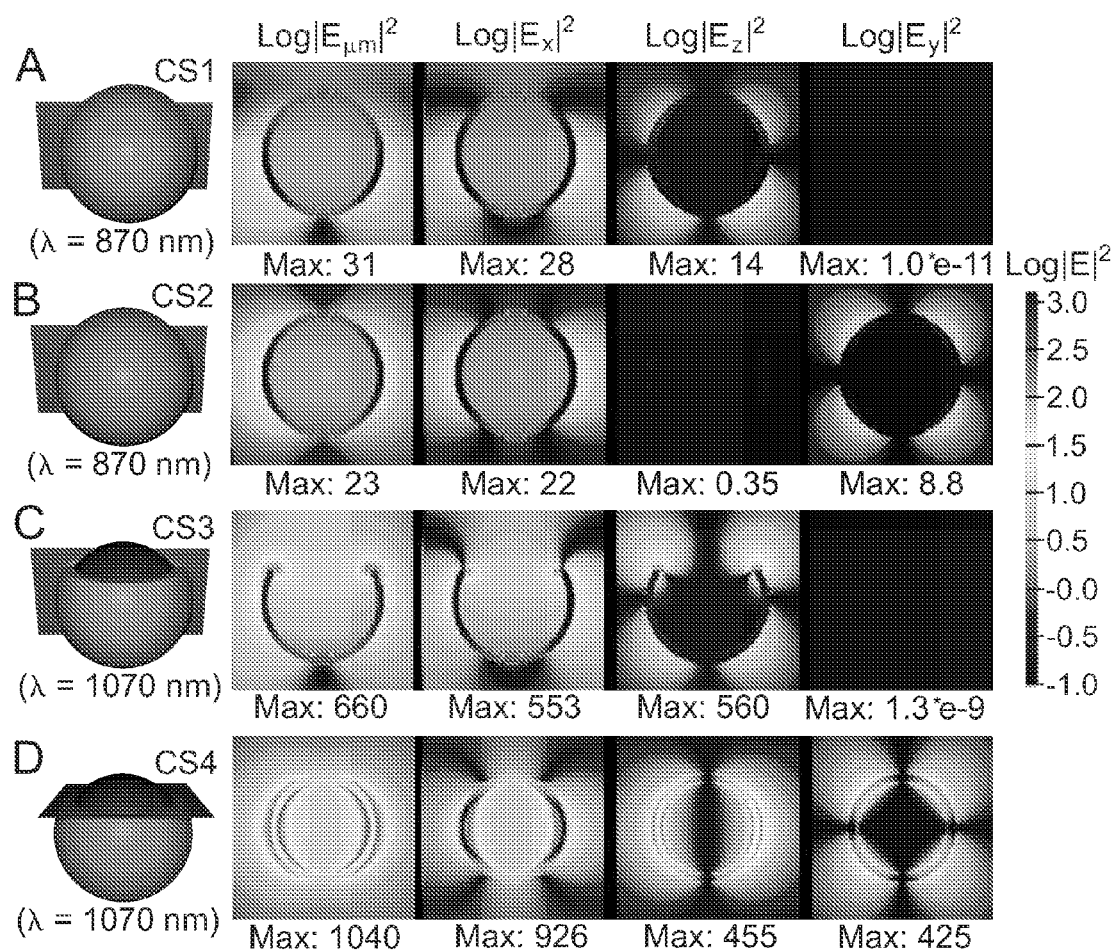
FIG. 3 shows finite difference time domain (FDTD) simulations of optical extinction spectra and near-field distribution pictures of nanoshells and open-nanoshells according to embodiments of the present invention.
Figure 10:
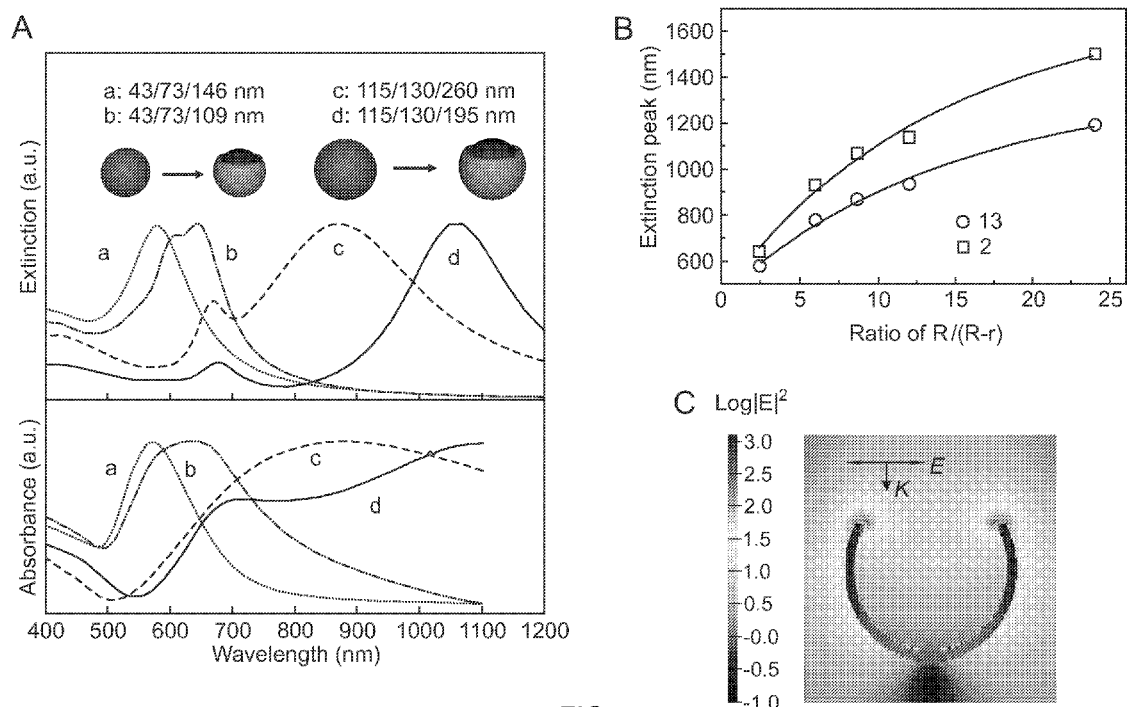
FIG. 10 (A) shows normalized theoretical (top) and experimental (bottom) optical extinction spectra of Au nanoshells (a, c) and open-nanoshells (b, d) monolayer structures in air according to embodiments of the present invention. (B) Theoretical extinction peaks of Au nanoshells and open-nanoshells with different ratios of particle radius and shell thickness in air. (C) Local electric field intensity ($\log|E|^2$) around open-nanoshell d at an extinction peak (1070 nm) in air.

A full 3-dimensional FDTD calculation was executed in the simulation. Cross sections (CS) of electrical field distribution around a Au nanoshell (CS1 and CS2) and open-nanoshell (CS3 and CS4) are shown in FIG. 3. CS1 and CS3 are in the plane of Y=0 nm, CS2 is in the plane of Z=0 nm and CS4 is in the plane of Z=195 nm. The shown field is normalized with respect to the incident field amplitude. FIG. 3 shows X, Y, and Z components of the electric field intensity and its summation ($\log|E|^2$) from the cross sections (CS) of a Au (A, B) nanoshell (CS1 in the plane of Y=0 nm, and CS2 in the plane of Z=0 nm) and (C, D) open-nanoshell (CS3 in the plane of Y=0 nm, and CS4 in the plane of Z=195 nm). On bottom of each panel is the maximum value of electric field intensity ($|E|^2$) in each plot (380 nm×380 nm). Full 3-dimensional finite difference time domain (FDTD) calculation (see FIG. 10A) showed the local electric field intensity distribution around Au open-nanoshell in a plane vertically through the central axis. The incident wavelength was in resonance with the first symmetric mode ($\lambda=1279$ nm). The local electric field was essentially similar to that of Au nanoshell in a same size around outer shell regions, but was substantially enhanced at the upper edge of the open-nanoshell with a maximum enhancement factor of ~19 with respect to the incident light field. The field distribution in a plane horizontally along the height of the non-removed shell of an open-nanoshell (FIG. 10B) showed that the uniform enhancement was maintained through the whole region of the edge surface. The highest field regions were located at the inner and outer wall edges with a maximum enhancement factor of ~23, where a plasmon resonance mode was similar to the case of nanoaperture structures with a strong electromagnetic coupling between the inner and outer wall edges, indicating a buildup of charge at two edges which supports the field enhancement uniformly on the edge surface. Even compared to Au nanoshells, the local electric field enhancement around Au open-nanoshells was improved 4 times (FIG. 3), which points to Au open-nanoshells as a very promising substrate for SERS-based biomolecules detection The optical properties of the open-nanoshell structures and the difference between the open-nanoshell and full shell particles were assessed by full 3-dimensional finite difference time domain (FDTD) calculations and spectrally resolved UV/VIS absorbance measurements. FIG. 10A compares the simulated extinction spectra (top) and the measured spectra (bottom) for two different nanoshell sizes. The simulated and measured spectra show a fair agreement; the remaining discrepancies are most likely attributable to the polydispersed size and inherent rough shell surface of Au open-nanoshells. The spectra furthermore indicate an interesting trend: removing the top of the nanoshell results in a pronounced red-shift of the plasmon resonance. This is corroborated by FIG. 10B, which shows the theoretical dependence of the extinction peak on the ratio between the core size and the shell thickness, for both open and closed nanoshells. The red-shift of the resonance is consistent and becomes more pronounced as this ratio increases. The resonance still has a dipolar character but is dominated by the local charge-build-up at the edges of the open-nanoshell, as indicated in FIG. 10C, which shows the electric field profile of the nanostructure at resonance conditions. This charge build-up is accompanied by a strong enhancement of the local electric field, as compared to the local enhancement of closed nanoshells. This has interesting prospects for surface enhanced Raman scattering (SERS), which strongly depends on the local electromagnetic enhancement.

Example 3

Figure 4:
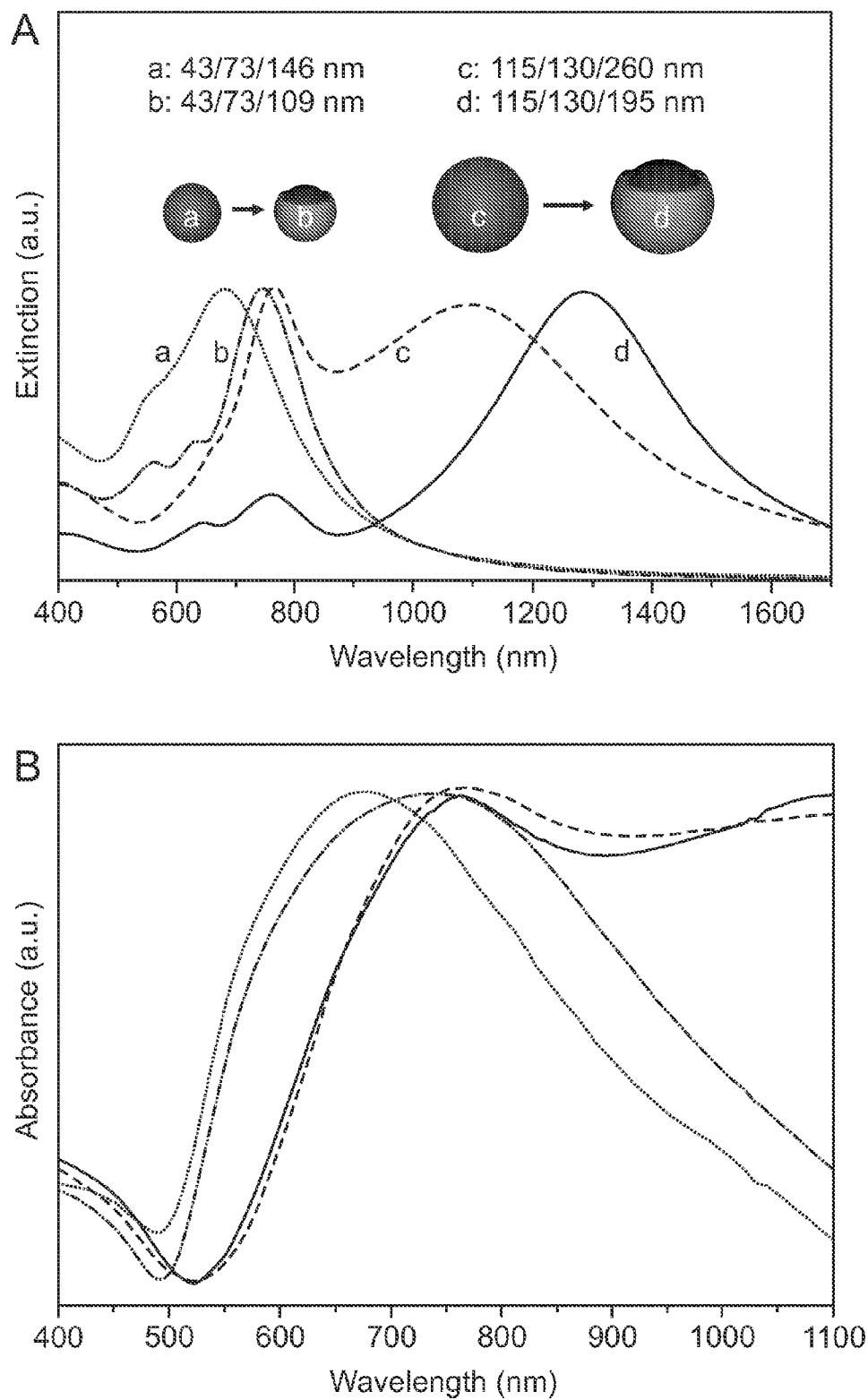
FIG. 4: normalized simulated optical extinction spectra (A) and experimental optical extinction spectra (B) for an aqueous suspension of Au nanoshells and Au open-nanoshells according to embodiments of the present invention.

Optical properties of Au open-nanoshells suspensions and monolayer structures have been studied experimentally (see below) and theoretically with FDTD simulations see above (FIG. 4).

Optical extinction spectra of ITO glass with monolayer structures of Au nanoshells or open-nanoshells were measured. All experimental optical extinction spectra were measured using a Shimadzu UV-1601PC spectrophotometer with a slit width of 2 nm and a data interval of 0.5 nm. An ITO glass with monolayer structures of Au nanoshells or open-nanoshells was orientated perpendicularly to the incident light during the measurement in air. The aqueous suspension of Au nanoshells and Au open-nanoshells were measured in the cuvettes (Eppendorf UVette).

FIG. 4 shows normalized simulated optical extinction spectra (A) and experimental optical extinction spectra (B) for an aqueous suspension of (a, c) Au nanoshells and (b, d) Au open-nanoshells. All simulated extinction spectra were calculated from FDTD calculations. All particles dimensional parameters are shown in the insets of (A).

FIG. 4 shows that with respect to Au nanoshells, open-nanoshells display an apparent red-shift of plasmon resonance in water or air, for example, from 675 nm for Au nanoshells (r/R/H=43/73/146 nm) suspensions to 730 nm for Au open-nanoshells (r/R/H=43/73/109 nm) suspensions (FIG. 4A), which can probably be explained by the fact that the inner edge interacts strongly with the outer edge in Au open-nanoshells. With the increasing of the ratio of core size and shell thickness of the open-nanoshell, the red-shift becomes more notable, since the interaction between the inner and outer edges becomes stronger. Because of a surrounding refractive index change and a random orientation, the extinction spectra of open-nanoshells in water show a feature of red-shift and broadening compare to those in air as expected.

A general agreement between the experimental and theoretical optical extinction spectra was found and the discrepancies are most likely attributable to the polydisperse size and inherent rough shell surface of Au open-nanoshells.

Due to the difficulty to make Au nanoshells with a small core size (<100 nm) and a thin shell thickness (<10 nm), Au open-nanoshells are advantageous as their features of optical response in near-infrared (NIR) region as well as their particle size remaining relatively small lead to suitable applications, such as the biomedical imaging and thermotherapy for certain tumour with a size requirement.

It is to be understood that although preferred embodiments, specific constructions and configurations, as well as materials, have been discussed herein for devices according to the present invention, various changes or modifications in form and detail may be made without departing from the scope and spirit of this invention. For example, any formulas given above are merely representative of procedures that may be used. Functionality may be added or deleted from the block diagrams and operations may be interchanged among functional blocks. Steps may be added or deleted to methods described within the scope of the present invention.

What is claimed is:

1. A method for fabricating a substrate having a layer thereon, said layer comprising nanoparticles, said nanoparticles comprising a conductive open shell, wherein substantially all of said nanoparticles have an open part of their shell away from said substrate, said method comprising the steps of:
    (i) providing nanoparticles comprising a dielectric core and a complete conductive shell around the core,
    (ii) depositing a layer of said nanoparticles on a substrate surface, and
    (iii) removing part of said conductive shell at an area of said nanoparticles away from said substrate surface thereby forming nanoparticles comprising a conductive open shell.

2. The method according to claim 1, said method further comprising a step, between step (ii) and step (iii), of coating said substrate surface having nanoparticles thereon with a fluid coating able to form a solid matrix embedding said nanoparticles, and wherein step (iii) comprises, after said solid matrix is formed, removing a part of said solid matrix at a surface thereof facing away from said substrate, thereby removing said part of said conductive shell.

3. The method according to claim 1, wherein the nanoparticles provided in step (i) are comprised in a fluid coating able to form a solid matrix embedding said nanoparticles, and wherein step (iii) comprises, after said solid matrix is formed, removing a part of said solid matrix at a surface thereof facing away from said substrate, thereby removing said part of said conductive shell.

4. The method according to claim 1, wherein the removing step is performed via a directional removing technique.

5. The method according to claim 2, wherein the directional removing technique is a directional etching technique.

6. The method according to claim 3, wherein the directional removing technique is ion milling.

7. The method according to claim 1, wherein prior to the depositing step, the substrate is chemically functionalized.

8. The method according to claim 1, further comprising a step of removing said dielectric core from said nanoparticles comprising a conductive open shell.

* * * * *